United States Patent [19]
Colin et al.

[11] Patent Number: 5,925,573
[45] Date of Patent: Jul. 20, 1999

[54] METHOD AND DEVICE FOR THE DETERMINATION OF AN ANALYTE USING SUPER PARAMAGNETIC REACTIVE PARTICLES

[75] Inventors: Bruno Colin, Marcy L'Etoile; Alain Theretz, Ecully, both of France

[73] Assignee: Bio Merieux, Marcy L'Etoile, France

[21] Appl. No.: 08/732,447

[22] PCT Filed: Mar. 20, 1996

[86] PCT No.: PCT/IB96/00245

§ 371 Date: Dec. 13, 1996

§ 102(e) Date: Dec. 13, 1996

[87] PCT Pub. No.: WO96/29601

PCT Pub. Date: Sep. 26, 1996

[30] Foreign Application Priority Data

Mar. 21, 1995 [FR] France .................................. 95 03528

[51] Int. Cl.$^6$ ..................... G01N 33/553; G01N 33/546; C12M 1/34; B03C 1/00
[52] U.S. Cl. .................... 436/525; 436/534; 436/806; 435/287.2; 435/283.1; 209/213; 209/214; 210/695; 210/222
[58] Field of Search .................. 435/287.2, 7.2, 435/7.1; 436/526, 534, 806; 422/68.1; 209/214, 213; 210/695, 222

[56] References Cited

U.S. PATENT DOCUMENTS

| | | |
|---|---|---|
| 3,985,649 | 10/1976 | Eddelman . |
| 4,913,883 | 4/1990 | Imai et al. . |
| 5,445,970 | 8/1995 | Rohr ........................................ 436/526 |
| 5,445,971 | 8/1995 | Rohr ........................................ 436/526 |

FOREIGN PATENT DOCUMENTS

| | | |
|---|---|---|
| 0 339 623 | 11/1989 | European Pat. Off. . |
| 0 357 786 | 3/1990 | European Pat. Off. . |
| 63-108264 | 9/1988 | Japan . |

Primary Examiner—James C. Housel
Assistant Examiner—S. Devi
Attorney, Agent, or Firm—Oliff & Berridge, PLC

[57] ABSTRACT

A process for the qualitative and/or quantitative determination of an analyte in a sample. The process includes providing a sample containing an analyte of interest in a liquid phase, providing at least one reagent having superparamagnetic reactive metal particles linked to a substance that binds to the analyte, contacting the sample and the reagent to allow binding of the analyte in the sample and the reagent, applying a magnetic field to the mixture of sample and reagent, and detecting the presence of the analyte in the sample. The device includes a support for the sample and reagent, means for contacting the sample and reagent, magnetic means for confining and separating the analyte from the other components of the sample, and detection means for qualitative and/or quantitative measurement of the analyte.

31 Claims, 3 Drawing Sheets

METHOD AND DEVICE FOR THE DETERMINATION OF AN ANALYTE USING SUPER PARAMAGNETIC REACTIVE PARTICLES

FIELD OF THE INVENTION

The present invention relates to the qualitative and/or quantitative determination of an analyte liable to be present in a sample.

BACKGROUND

According to the invention, the term "determination of an analyte" is intended to mean the detection and/or assaying of any biochemical or biological substance, and in particular living matter, for example bacterial cells. In the latter case, the quantitative determination may consist in counting the bacterial cells.

However, according to the present invention, the analyte to be determined may also be, without limitation, an antigen, a hapten, an antibody; a peptide, a fragment of nucleic acid (DNA) or (RNA), an enzyme or a substrate, on condition that the analyte in question generally comprises a ligand having at least one recognition site which can bind specifically to a determined anti-ligand.

As used in the present invention, the terms ligand and anti-ligand refer to any biological or biochemical molecules capable of forming a ligand/anti-ligand complex, such as the following complexes: antigen/antibody, antibody/hapten, hormone/receptor, protein/antibody, biotin/streptavidin, lectin/sugar, chelating agent/chelated molecule, oligonucleotide/oligonucleotide hybrid, olinucleotide/nucleic acid hybrid, or enzyme/substrate; it being understood that, when the ligand is a nucleic acid fragment, it may equally well be an RNA fragment or a DNA fragment.

According to the invention, the term "antibody" is intended to mean monoclonal antibodies, polyclonal antibodies, antibody fragments and antibodies obtained by genetic recombination.

Patent Application EP-0,339,623 describes and proposes a process for the determination of an analyte in a sample, according to which:

i) the sample is presented in the liquid phase, in which the analyte comprises a ligand having at least one site for specific recognition of an anti-ligand;

ii) at least one reagent is presented, comprising super-paramagnetic reactive metal particles in suspension in the liquid phase, each reactive particle comprising a metal core on which at least one said anti-ligand is bound directly or indirectly;

iii) the sample and the reagent are brought into contact, in particular by incubation, in order to obtain, in the liquid phase, an intermediate mixture of metal complexes of the reactive particles which have reacted with the analyte, and unreacted residual reactive particles;

iv) a magnetic field is applied to the intermediate mixture in order to subject the latter to magnetophoresis, which causes differentiated migration of the metal complexes in the intermediate mixture, in the liquid phase and without physical separation of them from the unreacted residual reactive particles; and v) at a reference point in the intermediate mixture, located in the direction of the magnetic field and by diffraction of light, the appearance of metal complexes is detected, in order to obtain a detection signal representing the presence and/or the quantity of the said complexes, which signal is correlated with the presence and/or the quantity of analyte originally present in the sample.

The process according to document EP-A-0,339,623 has the drawback of resorting to a means for detecting the metal complexes which is particularly complicated because, in practice, it requires a coherent monochromatic light source (laser), a diffracted-light detector and processing of the light signal thus collected.

SUMMARY OF THE INVENTION

The subject of the present invention is a process which allows much simpler detection of the metal complexes.

According to the present invention, in combination:

a) according to step (iv), with the magnetic field applied to the magnetic mixture, on the one hand the metal complexes of the reactive particles which have reacted with the analyte are confined or collected, in the form of a measurement aggregate, and, on the other hand, the measurement aggregate is separated from the unreacted residual particles, by which term physical separation is meant; it being possible for the confinement and the separation of the metal complexes from the residual particles to be carried out simultaneously;

b) according to step (v), the separated measurement aggregate is detected by measuring its ferromagnetic mass resulting from the reaction of the super-paramagnetic reactive metal particles with the anti-ligand, and possibly from their agglutination, this ferromagnetic mass representing the presence and/or the total quantity of the metal complexes.

DETAILED DESCRIPTION OF PREFERRED EMBODIMENTS

According to the invention, use is made, in a manner which is known per se and as in document EP-A-0,339,623, of a reagent referred to in particular as a ferro-fluid, that is to say a reagent comprising super-paramagnetic reactive metal particles in suspension in the liquid phase. Each reactive particle in such a reagent comprises a metal core onto which at least one said anti-ligand is bound directly or indirectly. The essential characteristic of such a reagent is that, when they have not reacted with the ligand, the magnetic and/or magnetizable reactive metal particles cannot be separated individually from the liquid phase by magnetic means, and when they have reacted with the ligand, they are ferromagnetic and behave as an aggregated ferromagnetic mass.

A full description of such reagents, which are known per se, including the way in which they may be obtained, is given in document EP-A-0,339,823 and, more particularly, in the following passages of this published patent application:

page 5, lines 9 to 23;
page 6, line 14 to page 7, line 13;

without there being any need to incorporate other developments or explanations in the present description.

Several ways of separating the measurement aggregate from the intermediate mixture in which the unreacted residual particles remain may be envisaged:

firstly, it is possible to set, and in particular move, the actual magnetic field used for confining the metal complexes, in order to move the latter from and out of the intermediate medium;

secondly, it is possible to fix or immobilize the magnetic field used for confining the metal complexes, and to move the intermediate medium containing the residual particles away from the measurement aggregate. In order to do this, it is possible either to circulate the intermediate medium relative to the fixed magnetic field used for confining the metal complexes, or to draw off the intermediate medium, in particular by pumping or absorption in an absorbent, from the measurement aggregate which is retained by the magnetic field for confining the metal complexes, the said magnetic field remaining fixed as stated above.

By virtue of the invention, detecting the metal complexes becomes extremely simple, since it is sufficient to measure the ferromagnetic mass of the measurement aggregate. To this end, use may be made of various means which are well-known to the person skilled in the art. Preferably, the measurement aggregate is placed in front of an electromagnetic sensor which generates an electric measurement signal representing the ferromagnetic mass and consequently the presence and/or the quantity of the metal complexes formed between the reagent and the analyte.

Quantitative determination of the analyte may be carried out using various direct or indirect analysis methods. For example, in a technique referred to as competition, another, so-called competition reagent is presented, comprising super-paramagnetic reactive magnetic particles in suspension in the liquid phase, each reactive particle comprising a metal core onto which another ligand specifically recognized by the anti-ligand of the reagent is bound directly or indirectly.

A further subject of the invention is a device for the qualitative and/or quantitative determination of an analyte in a sample, comprising:

i) a support, in particular a container, for receiving the sample in the liquid phase, in which the analyte comprises a ligand having at least one site for specific recognition of an anti-ligand;

ii) a source of at least one biologically reactive reagent as defined above;

iii) means for bringing the sample and the reagent into contact, in particular by incubation, in order to obtain, in the liquid phase, an intermediate mixture of metal complexes of the reactive particles which have reacted with the analyte, and unreacted residual particles;

iv) a means for applying a magnetic field to the intermediate mixture;

v) a means for detecting the separated metal complexes, in order to obtain a detection signal representing the presence and/or the quantity of the complexes, which signal is correlated with the presence and/or the quantity of analyte originally present in the sample.

According to the present invention, in combination:

a) The means for applying the magnetic field according to (iv) comprises or is used as both the means for confining or collecting the metal complexes formed between the metal particles and the analyte, in the form of the measurement aggregate, and means for separating (which is intended to mean physically separating) the aggregate remaining on the support from the unreacted residual particles;

b) the detection means according to (v) comprises, on the one hand, a means for measuring the ferromagnetic mass, or magnetic mass, of the separated measurement aggregate, generating a measurement signal representing the presence and/or the total quantity of the metal complexes, and on the other hand a means for placing the support, with the measurement aggregate, in front of the measuring means.

As stated above, the reactive metal particles in suspension in the liquid phase consist of a reagent, in particular a ferro-fluid, onto which the anti-ligand, for example an antibody, is bound or grafted directly or indirectly.

By way of example, the metal core of the particles in the reagent is selected from magnetic materials which are intrinsically magnetic and/or magnetizable, such as the complex salts and the oxides, the borides and the sulfides of iron, of cobalt or of nickel and the rare-earth elements, which have a high magnetic susceptibility, such as hematite and ferrites. The metal core of the particles comprises pure metals or alloys comprising one or more of these elements. The metal core is preferably designed to have no residual magnetism and its mean size is between 5 and 30 nm, in particular 10 and 20 nm. The metal core may represent from 5 to 100% by weight, in particular 25 to 65% by weight, of the reactive particle.

The reactive metal particles may comprise a shell in addition to the metal core. The composition cl the shell is not critical, so long as it makes it possible to bind anti-ligands and it can interact with the metal core. By way of example, the shell may be a natural polymer, optionally chemically modified, for example, a polysaccharide such as agarose, dextran and cellulose derivatives such as carboxymethylcellulose; a protein such as gelatin and an albumin polymer; and a synthetic polymer, optionally chemically modified, such as acrylic or methacrylic acids.

The mean size of the reactive particles is between 20 and 100 nm, in particular between 50 and 70 nm.

The process and the device according to the invention are more particularly beneficial for the determination of an analyte, such as a bacterial cell, in low concentration in a sample. In effect, there is not yet a method which is sufficiently sensitive for directly detecting a few bacterial cells in a sample, so that it is necessary to employ an enrichment step beforehand.

The reagent or reagents is or are mixed with the liquid sample which is assumed to contain the analyte and therefore the ligand, then the mixture is subjected, for example, to incubation. The sample and the reagent are brought into contact at a determined pH which depends on the nature of the ligand to be detected. Although the contact may take place in a very wide temperature range, from 2 to 95° C., the temperature advantageously selected is room temperature or a temperature between 37° C. and 40° C. The contact time is determined as a function of the time of qualitative and/or quantitative determination, using conventional operating conditions which are known per se.

A buffer is normally used for maintaining the desired pH. The buffer solution which can be used may be selected from a phosphoric acid buffer or a Tris buffer, etc. In some cases, salts, proteins or detergents are added to the mixture of the reagent of the sample, in order to prevent non-specific reactions.

BRIEF DESCRIPTION OF THE DRAWINGS

The invention will be described in conjunction with the following drawings in which like reference numerals designate like elements and wherein.

Figure 1:
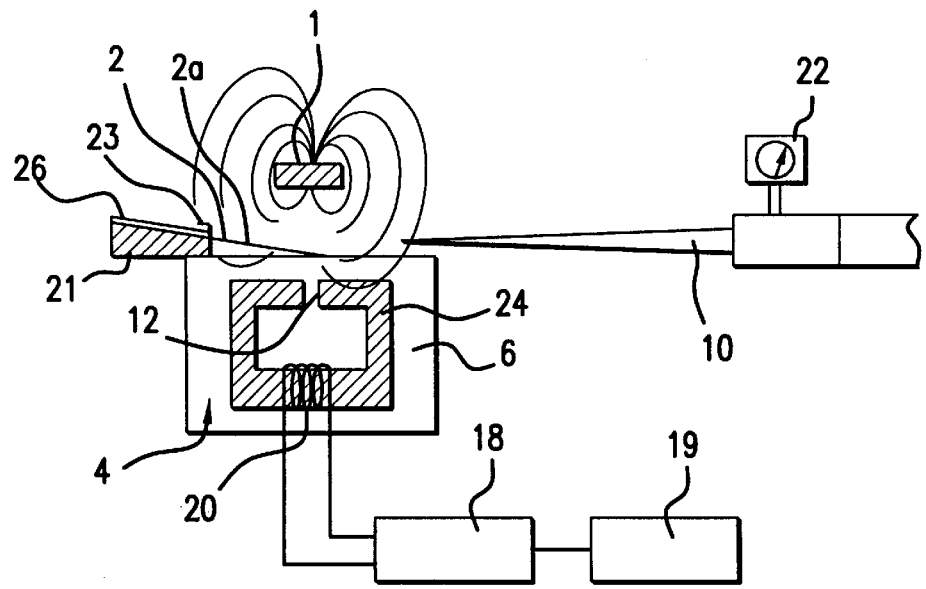
FIGS. 1, 2, 3, 4 and 5 schematically depict devices according to the invention.

The underlying principles of the present invention will first be explained on the basis of the experimental protocol described below.

Synthesis of $Fe_3O_4$/Dextran T40 (50%) particles 14 grams of Dextran T40 (Mw=40,000, Pharmacia) are added to 15 ml of water, and the Dextran is left to dissolve at room temperature in order to form a first solution.

A second solution is prepared with 3 grams of $FeCl_3.6H_2O$ (Mw=270.30) and 1.3 grams of $FeCl_2.4H_2O$ (Mw=198.81) in 20 ml of water.

The two solutions are introduced into a 250 ml double-walled reactor equipped with a stirring motor set to about 200–250 rpm, a glass stirrer and a dropping funnel containing a 7.5% (v/v) $NH_4OH$ solution.

At room temperature, the 7.5% (v/v) $NH_4OH$ solution is added dropwise to a final pH of between 10 and 11. The reactor is heated to 70° C. for about 60 minutes. At the end of the reaction, the solution is recovered and dialyzed extensively against 5 l of distilled water, then filtered on quartz wool. This solution is then centrifuged 3 times at 600 rpm for 5 minutes.

In order to remove the unreacted Dextran the particles are deposited on a 33×2.5 cm column of SEPHACRYL S300 HR gel (Pharmacia)(a cross-linked copolymer of allyl dextran and N,N'-methylenebisacrylamide), equilibrated beforehand using a pH 6.5 buffer comprising 0.1M acetate, 0.15M NaCl and 0.05% $NaN_3$.

The metal particles in the ferro-fluid which is obtained have an external diameter of between 20 and 900 nm, and preferably between 50 and 70 nm, with a Dextran shell. They are stored at +4° C.

Preparation of reactive particles carrying at least one antibody directed against Listeria, hereafter referred to anti-L Ab.

The particles synthesized according to the example above are oxidized by adding sodium periodate (0.1 M).

After stirring for 45 minutes, in the absence of light, the particles are subjected to dialysis against 0.15 NaCl for 4 hours.

10 μ/ml of anti-L Ab are added to the solution containing the metal particles, the concentration of which is 1 mg of particles per mg of reagent. The pH is adjusted to about 8 by adding $NaHCO_3$.

The mixture is incubated for 20 hours, with gentle stirring. The mixture thus formed is reduced by adding a sodium borohydrate solution at a concentration of $12 \times 10^{-3}$ mols of $NaBH_4$ per mg of particles, with gentle stirring for 45 minutes. The mixture is dialyzed overnight against a pH 7.5 buffer comprising sodium phosphate (0.1M) and NaCl (0.15M).

The final solution contains 0.415 mg of metal particles per ml of reagent and 15.4 μg of anti-L Ab per mg of particles, i.e. about 6.4 μg of anti-L Ab per ml of reagent.

Qualitative and/or quantitative determination, in particular detection of Listeria bacteria using an electromagnetic sensor.

Referring to FIG. 1, the experimental set-up used comprises:

- a support 2, identical to that of a traditional audio or video recording tape, for example a $5 \times 10^{-2}$ mm thick polyester film. This support consists of a tape comprising, on the one hand, a fastening base 2b and a tongue 2a which is relatively free and, in particular, capable of being subjected to oscillations, in particular of vibrating using any suitable means, in particular under the effect of a tangential airflow defined below. This impermeable support is intended to receive, in the liquid phase, the sample to be treated which comprises the bacterium to be assayed, and/or the reagents prepared as above, and/or the intermediate mixture comprising the metal complexes consisting of reactive particles which have reacted with the bacteria considered as being the analyte;
- a fixed means 21 making it possible to fix the support defined above, for example using two hooks 23;
- a means 4 for detecting metal complexes, in the form of a confined and separated measurement aggregate as defined above and supported by the support 2. According to the invention, this detection means 4 is a means for measuring the ferromagnetic mass of the separated measurement aggregate and comprises an electromagnetic sensor 6 which generates an electric measurement signal, for example a detection electromotive force, representing the ferromagnetic mass of the separated measurement aggregate, and consequently the presence and/or the total quantity of metal complexes. This sensor is formed, in traditional fashion, as in the case of the read head for an audio or video recorded tape, by a magnetic circuit 24 defining a magnetic air gap 12, at a distance from which and in front of which the tongue 2a of the support 2 is arranged. A coil 20 is arranged between the two limbs of the magnetic circuit 24 which has a U-shape in cross section;
- a system for processing the electric measurement signal at the output of the coil 20, comprising an amplifier 18 whose gain can be adjusted, and a display 19 at the output of the amplifier 18;
- a permanent magnet 11, or auxiliary magnetic generator, located above the electromagnetic sensor 6 in order to increase the measurement signal at the output of the sensor 6, and more precisely of the coil 20;
- a means for oscillating or vibrating the tongue 2a in a vertical direction, consisting of a nozzle 10 which projects a flow of an inert gas focused on the edge or the side of the tongue 2a. The intensity of the gas flow is regulated by monitoring the pressure of the gas in the nozzle 10, using a manometer 22. The vibration means 10 may be an electromagnetic means.

Depending on the intensity of an airflow projected by the nozzle 10, measured in arbitrary units, for example the graduations of the manometer 22, the output voltage 19 is measured for various configurations, namely:

- without a tongue 2a in front of and at a distance from the magnetic air gap 12, i.e. $V_0$;
- in the presence of the tongue 2a or support 2, but without reagent, still at a distance from and in front of the air gap 12, i.e. $V_b$;
- and, finally, with a predetermined quantity of reagent, in front of and at a distance from the air gap 12, i.e. V.

For this first trial, the gain of the amplifier 18 is fixed at the value 4.2.

Regardless of the intensity of the airflow applied tangentially with respect to the air gap 12, the voltage displayed at 19 remains substantially the same, whether or not a support 2 is present in front of the air gap 12.

Above an airflow of 52 (arbitrary value corresponding to a pressure of about 150 millibar), the voltage displayed with the magnetic support, i.e. "V", increases strongly since it changes from 18 mV to 50 mV between 11 and 51 for the airflow, and from 50 to 190 mV at 52, reaching a maximum at 62.

The value of the airflow adopted for the following trials is consequently close to 62.

Next, with the same airflow fixed at the value 62, the maximum and minimum displayed voltages $V_0$, $V_b$ are determined as a function of the gain of the amplifier 18. It is thus observed that, in order to detect a significant signal, the gain of the amplifier 18 must be greater than 4.

With the two values thus determined, respectively of the airflow, i.e. 62, and of the gain of the amplifier, i.e. 4, the signal/noise ratio is then optimized, this ratio being expressed by the equation $$\frac{V_m - V_o}{V_b - V_o}$$

in which $V_m$ is the voltage displayed at 19 for a measurement.

Firstly, by using a support 2, one μl of ferro-fluid, identical to the metal particles considered above but before binding an anti-ligand or anti-body, are deposited together with *E. coli* bacteria on this support 2. During incubation, it is observed that the measured voltage Vm remains substantially constant, and on average equal to 11.95, to within 1.1%, with a standard deviation of 0.13. This voltage is not very different from the voltages $V_0$ and $V_b$ obtained under the same experimental conditions, so that the signal/noise ratio is not very great.

By varying the gain of the amplifier 18 once more, it is determined that the signal/noise ratio is optimal for a gain of 6, while keeping the same intensity of the airflow which vibrates the support 2. Under these conditions, by using a support 2 of the audio/video magnetic tape type, to which 1 μl of the reagent prepared above is applied, comprising 0.5 mg per ml of ferro-fluid with 0.5 μl per ml of anti-Listeria antibody, the signal/noise ratio obtained is 140.

Keeping the same airflow and the same gain, with a support 2 of the audio/video magnetic tape type, the difference between the measured voltage Vm and the voltage Vb is measured, respectively with one μl of water, 1.46 ng of ferro-fluid not coated and not ligated to the antibody, 14.6 ng, 146 μg and 1.46 μg of the same ferro-fluid. The values collated in the table below are thus obtained.

|  | $V_m$ | $V_m - V_b$ |
|---|---|---|
| $v_0$ | 10.2 |  |
| $V_b$ | 10.6 |  |
| water | 11.2 | 0.6 |
| 1.46 ng | 10.7 | 0.1 |
| 14.6 ng | 12.3 | 1.7 |
| 146 ng | 11.9 | 1.3 |
| 1.46 μg | 15.3 | 4.3 |

This table shows that the smallest detectable quantity of reagent is 14.6 ng, it being seen that the displayed signal does not increase proportionately with the quantity of reagent.

Still with the same conditions regarding the airflow and the amplification gain, and a support 2 of the magnetic tape type, the voltages $V_0$, $V_b$ and $V_m$, as well as the signal/noise ratio, are determined successively when the support comprises an intermediate mixture consisting of the complex formed between the reagent prepared above and a sample in the liquid phase containing [$10e^9$] per ml of Listeria bacteria. Under these conditions, the voltage $V_m$ obtained is 530 mV and the signal/noise ratio is 113. This ratio can be increased by reducing $V_b$, for example by reducing the intensity of the airflow injected through the nozzle 10. For example, and in the case of Listeria bacteria, the airflow can be set to a value of 44 (using the arbitrary units defined above) in order to obtain the smallest signal detectable with the aforementioned bacteria. Under these new conditions, for the same concentration of bacteria in the liquid-phase sample, and with a reagent present on the support, in contact with the sample, in a proportion of 5 μg/ml of antibody and 1 mg/ml of ferro-fluid, an output signal of 700 mV is obtained with a signal/noise ratio of 1714.

This experimental protocol therefore demonstrates that it is possible, according to the invention, to obtain an output signal that can be correlated with the presence and/or the quantity or number of bacteria present in the sample to be assayed or detected, that is to say a measurement signal.

According to the appended drawings, comprising schematic FIGS. 2 to 5, various devices for qualitative and/or quantitative determination according to the present invention are illustrated.

According to FIG. 2, a device 1 according to the invention comprises:

i) an impermeable support 2, moved in translation in the direction and the sense 74, making it possible to receive the sample in the liquid phase, for example an inoculum deposited on the support 2 in a receiving region 8;

ii) a source of the reagent defined above being provided, for bringing the said reagent into contact with the said sample, for example in the region 8;

iii) this contact, in particular by incubation, of the sample and of the reagent making it possible to obtain in the liquid phase, for example in the region 8, the intermediate mixture defined above;

iv) a means 3 for applying the magnetic field used both as a means for confining the metal complexes defined above, in the form of a measurement aggregate, and as a means for separating, on the support, the said aggregate from the unreacted particles, this means 3 consisting of a permanent magnet arranged transversely relative to the support 2 which is in the form of a tape;

v) a means 4 for detecting the metal complexes thus confined and separated, comprising the electromagnetic sensor 6 for detecting the ferromagnetic mass of the measurement aggregate having a magnetic air gap 12, in order to obtain a measurement signal 5 which can be displayed at 13 and represents the magnetic mass of the aggregate, and thereby the presence and/or the quantity of metal complexes, which can be correlated with the quantity of analyte originally present in the sample.

According to the present invention, and in combination:

a) the detection means 4 according to (v) comprises, on the one hand, the means 6 for measuring the ferromagnetic mass, which generates the measurement signal 5 which is electrical in nature and represents the presence and/or the total quantity of the metal complexes originally present in the aforementioned intermediate mixture; and the support 2 in the form of tape constitutes a means for presenting these confined and separated metal Complexes by passing them in front of and at a distance from the electromagnetic sensor 6 located below the support 2;

b) the means 3 for applying the magnetic field according to (iv), in this case the transverse permanent magnet, is used both as the means for confining the metal complexes, collecting them in the form of a measurement aggregate, and as a means for separating the said aggregate by transporting it from the receiving region 8 to a separation region 9, in order to obtain, in the latter, the said aggregate in the separated state, which can then be detected by the electromagnetic sensor 6, by presenting it or passing it at a distance from and in front of this sensor.

As stated above, the support 2 is flat and consists, for example, of a tape which is impermeable to the sample, the reagent and the intermediate mixture in the liquid phase. Its upper surface is such that the liquid phase of the reaction partners can slide or flow from one region to another, for example from the receiving region 8 which receives at least the intermediate mixture, to the separation region 9 for separating the measurement aggregate, under the effect of the magnet 3 which generates a magnetic field making it possible, in particular, to transfer the measurement aggregate from the first region to the separation region.

As in the experimental set-up described with reference to FIG. 1, vibrations of the support 2 are generated, in a direction which is vertical relative to the horizontal plane of the said support, which vibrations are transmitted to the measurement aggregate when it passes in front of and at a distance from the electromagnetic sensor 6. As described above, this generator may consist of a means 10 for projecting a tangential gas flow against the edge or the side of the support 2.

An auxiliary magnetic generator 11 is arranged at the electromagnetic sensor 6 so as to increase the detection signal generated by the latter.

The process for qualitative and/or quantitative determination of an analyte, for example a bacterium, in a sample, derives from the above description and comprises the following steps:

i) the sample in the liquid phase is arranged in the receiving region 8 ii) the reagent defined above is introduced into this region 8;

iii) by incubation, contact between the sample and the reagent in the region 8 is allowed to be established, in order to obtain, in the liquid phase, the intermediate mixture which comprises both the metal complexes and the unreacted residual reactive particles;

iv) using the magnetic field which is generated by the magnet 3 and is applied to the intermediate mixture, the metal complexes are confined in the form of a measurement aggregate, and the said aggregate is separated from the unreacted particles by transferring this aggregate 7 from the receiving region 8 to the separation region 9, in order to obtain, in the latter, a separated measurement aggregate 7 which can be detected by the electromagnetic sensor 6 by passing it in front of and at a distance from the latter;

v) the measurement aggregate 7 thus separated is detected by measuring its ferromagnetic mass, by presenting the said aggregate in front of the electromagnetic sensor 6 which generates an electric measurement signal 5 representing the presence and/or the quantity or total number of the aforementioned metal complexes.

On the supports 2 moving in translation along the arrow 74, there are therefore, so to speak, two tracks: the first, reaction track 26 and the second, measurement track 27, in relation to which the electromagnetic sensor 6 is arranged under the tape or support 2.

As described above, by virtue of the magnet 3, the metal complexes are confined and separated or extracted selectively from the receiving region 8 and transferred to the second, separation region 9, and consequently, so to speak, transferred from the first track 26 to the second track 27, this being done under the effect of the magnetic field generated by the magnet 3, focusing the magnetic lines on the separation region 9. This transfer takes place in the flat stage, on the support 2.

Since the flat support 2 is subjected to periodic oscillations in the vertical direction, under the effect of the gas jet which is emitted by the nozzle 10 and encounters the edge of the support 2, the measurement aggregate 7 is itself subjected to oscillations or vibrations in front of the electromagnetic sensor 6.

Furthermore, in order to increase the detection signal 5, an auxiliary magnetic field is applied at the sensor 6 by virtue of the magnet 11. Such a magnet is, for example, a neodymium-iron-boron magnet (diameter 6 mm, height 5 mm), the resonance of which is more than 30% and the energy efficiency of which is 70%.

Figure 2:
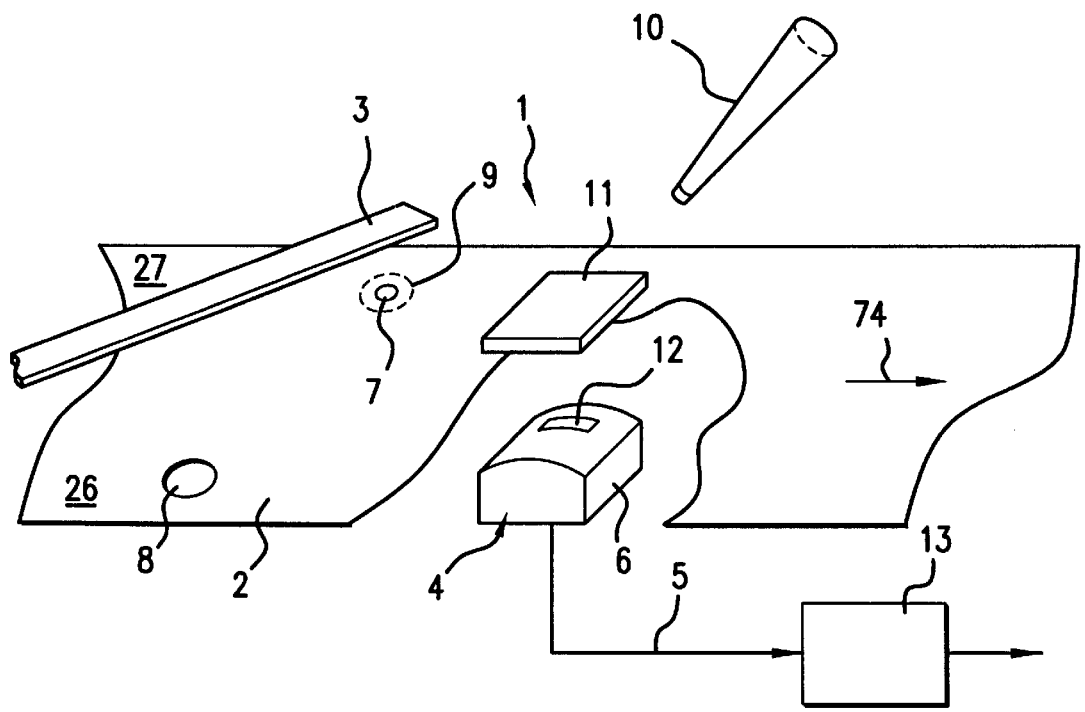
Figure 3:
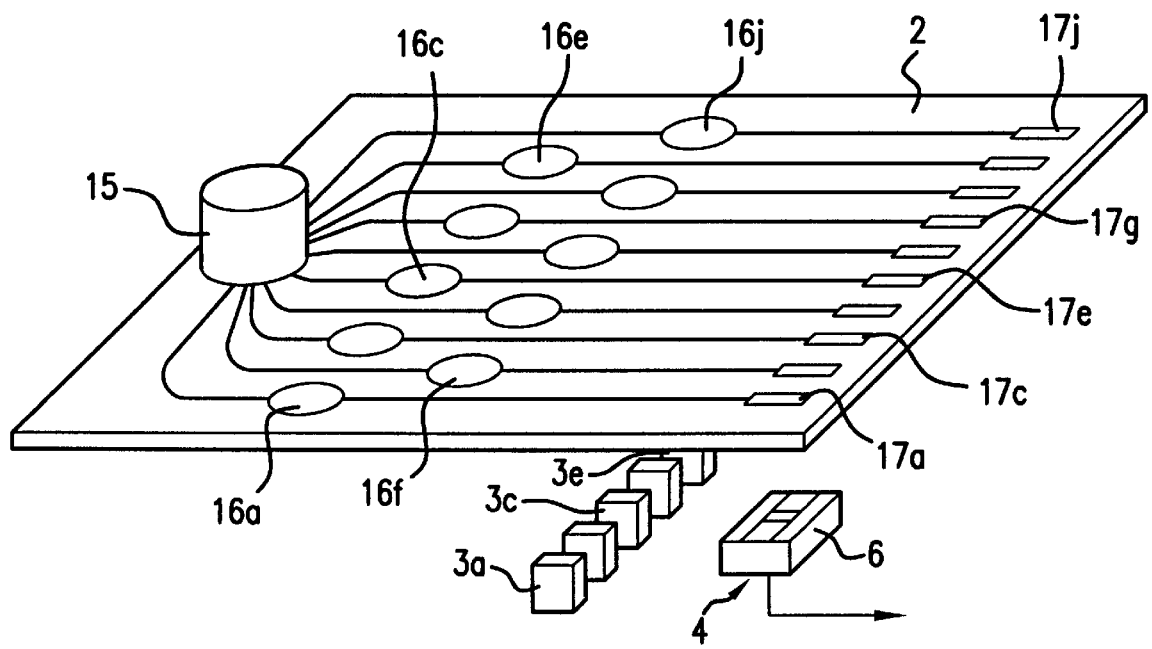

The device represented in FIG. 3 differs from the one represented in FIG. 2 in that it consists of a card which makes it possible to use a single biological sample to carry out a plurality of biological or biochemical determinations. To this end, the support 2 consists of a molded card which comprises:

a well 15 for receiving the sample in the liquid phase, a plurality of incubation wells 16a to 16j, connected in parallel to the single receiving well 15, each of which forms a first region for receiving a portion of the sample, the reagent and the intermediate mixture once formed;

a plurality of reading wells 17a to 17j connected respectively to the various incubation wells 16a to 16j and each forming a second region for separation of a measurement aggregate;

a plurality of magnets 3a to 3j arranged in correspondence with the plurality of channels which respectively join the receiving wells to the reading wells, for transferring the intermediate complexes;

and a single electromagnetic sensor 6 which can be moved in front of the various reading wells 17a to 17j, respectively.

Figure 4:
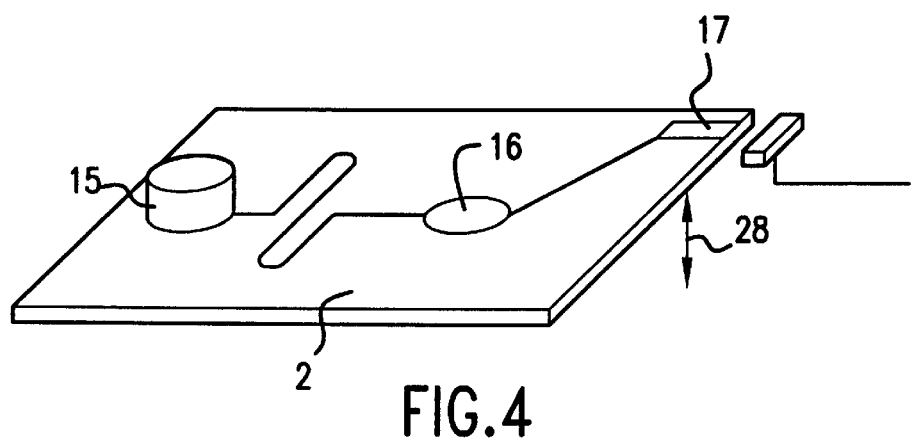

The device represented in FIG. 4 differs from the ones respectively represented in FIGS. 2 and 3 in that:

on the card or sleeve forming the support 2 there is a single incubation well 16 which contains the reagent prepackaged in the liquid phase;

the receiving well 15 is connected to the incubation well 16 by a channel which is leaktight to the sample in the liquid phase and to the reagent in the liquid phase when the support 2 is not vibrated flat in the direction 28, and allows the same sample to pass when the support 2 is vibrated in the same direction;

there is a single reading well 17, connected to the incubation well 16 by a straight channel, whereas the channel joining the wells 15 and 16 has a zig-zag flat shape.

Figure 5:
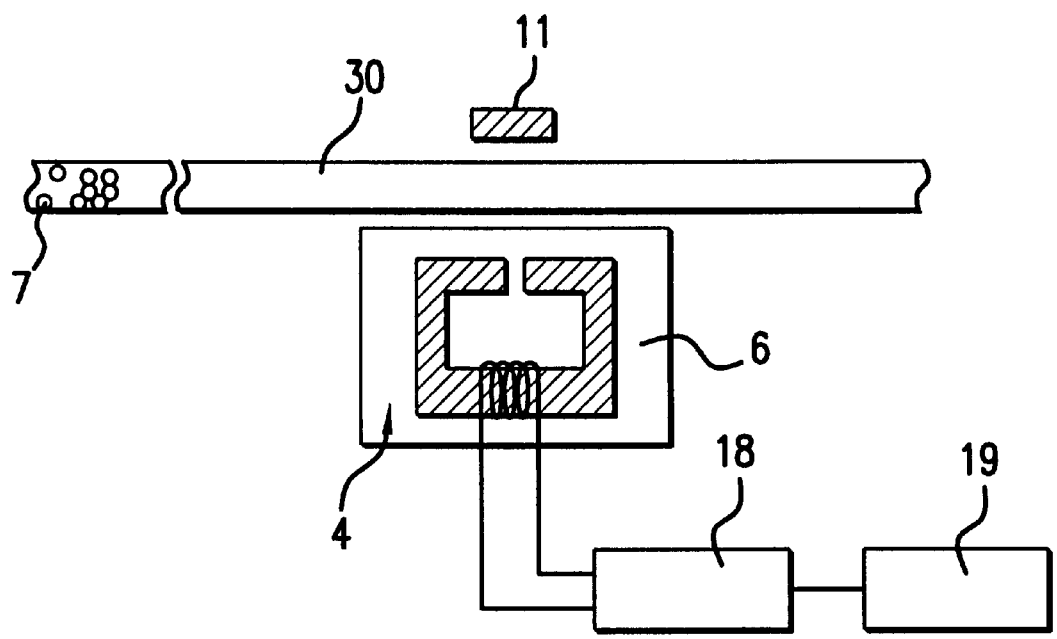

According to FIG. 5, and according to another embodiment of the present invention, the means for confining and separating the metal complexes is a conduit 30 for circulating the intermediate mixture, for example a capillary conduit, arranged in front of the electromagnetic sensor 6 or means for measuring the ferromagnetic mass of the measurement aggregate, the cross section of which is tailored to detection of the said mass by the said sensor.

According to this embodiment, the metal complexes are therefore confined and separated by circulating the intermediate mixture in a liquid stream passing in front of the electromagnetic sensor 6, the cross section of which stream is tailored to detection of the ferromagnetic mass of the measurement aggregate 7 by the sensor 6.

What is claimed is:

1. A process for determining the presence or quantity of an analyte in a sample, comprising:

i) providing said sample in a liquid phase, in which the analyte comprises a ligand having at least one site for specific recognition of an antiligand;

ii) providing at least one reagent comprising superparamagnetic reactive metal particles in suspension in a liquid phase, each reactive particle comprising a metal core onto which at least one said anti-ligand is bound directly or indirectly;

iii) contacting the sample and the reagent in order to obtain, in a liquid phase, an intermediate mixture of metal complexes of the reactive particles which have reacted with the analyte, and unreacted residual reactive particles;

iv) applying a magnetic field having magnetic lines to the intermediate mixture; and v) detecting the metal complexes in order to obtain a detection signal representing at least one of a presence and a quantity of said metal complexes, said signal being correlated with at least one of said presence and said quantity of said analyte originally present in the sample, wherein:

a) according to step (iv) with the magnetic field applied to the intermediate mixture, the metal complexes of the reactive particles which have reacted with the analyte are confined, in a form of a measurement aggregate, and said aggregate is separated from the unreacted residual reactive particles; and b) according to step (v), the separated measurement aggregate is detected by measuring its ferromagnetic mass representing at least one of the presence and the quantity of said metal complexes.

2. The process according to claim 1, wherein the measurement aggregate is separated from the intermediate mixture in which the unreacted residual reactive particles remain and said measurement aggregate is moved from, and out of, said intermediate mixture.

3. The process according to claim 2, wherein a support is provided having at least a first and a second region, wherein the intermediate mixture is present in the first region, and wherein the metal complexes are confined and separated by extracting the measurement aggregate from the first region containing the intermediate mixture, and said aggregate is transferred to the second region.

4. The process according to claim 3, wherein the extraction and transfer of the measurement aggregate, from the first region to the second region, take place under an effect of the magnetic field, in which the magnetic lines are focused on said aggregate.

5. The process according to claim 3, wherein the transfer of the measurement aggregate from the first region to the second region takes place in a plane, on a flat support which is impermeable to at least the intermediate mixture.

6. The process according to claim 1, wherein the measurement aggregate is separated from the intermediate mixture, in which the unreacted residual reactive particles remain, by fixing the magnetic field used for confining the metal complexes and by moving the intermediate mixture containing the unreacted residual reactive particles away from the measurement aggregate.

7. The process according to claim 6, wherein the intermediate mixture is present in a liquid stream that is moved past the magnetic field used for confining the metal complexes, and wherein said magnetic field traps said metal complexes while permitting the rest of said intermediate mixture to flow past.

8. The process according to claim 7, wherein
a means for detecting said metal complexes that can detect the presence or quantity of said metal complexes by assaying a cross-section of said liquid stream is provided, wherein said detection means can measure the ferromagnetic mass of the measurement aggregate, and wherein said process comprises passing the intermediate mixture in front of said detection means.

9. The process according to claim 6, wherein the intermediate medium is drawn off from the aggregate retained by the magnetic field for confining the metal complexes, and said aggregate remains fixed.

10. The process according to claim 1, wherein a measuring means is provided that can measure electromagnetic fields and wherein the ferromagnetic mass of the aggregate is measured by placing the measurement aggregate in front of the measuring means to generate an electric measurement signal representing said ferromagnetic mass.

11. The process according to claim 10, wherein an oscillating means is provided that imparts periodic oscillations to the measurement aggregate in front of the measuring means.

12. The process according to claim 5, wherein a measuring means is provided that can measure electromagnetic fields and wherein an oscillating means is provided, and wherein, in front of the measuring means, the flat support is subjected to periodic oscillations generated by said oscillating means.

13. The process according to claim 10, wherein a means for generating an auxiliary magnetic field is provided and wherein the process comprises applying, at the measuring means, an auxiliary magnetic field which increases the ferromagnetic mass of the measurement aggregate.

14. A device for the qualitative and/or quantitative determination of an analyte in a sample, comprising:

i) a support comprising a receiving region and a separating region, wherein the receiving region can receive said sample in a liquid phase, in which the analyte comprises a ligand which specifically recognizes an anti-ligand, said sample remaining unbound to said support;

ii) a source of at least one reagent comprising superparamagnetic reactive metal particles in suspension in a liquid phase, each of said reactive metal particles comprising a metal core on which at least one said anti-ligand is bound directly or indirectly;

iii) means for contacting the sample and the reagent in said receiving region on said support, in order to obtain, in a liquid phase, an intermediate mixture of unbound metal complexes of the reactive particles which have reacted with the analyte, and unreacted residual reactive particles;

iv) magnetic means adapted for confining the unbound metal complexes into an unbound measurement aggregate, and separating said aggregate from said receiving region and from the unreacted residual reactive particles; and v) detection means, physically separated from the receiving region on said support, for measuring the ferromagnetic mass of the separated measurement aggregate, and providing a measurement signal representing the presence and/or the total quantity of said metal complexes.

15. The device according to claim 14, wherein the detection means comprises an electromagnetic sensor which generates an electric measurement signal representing the ferromagnetic mass of the separated measurement aggregate.

16. The device according to claim 14, further comprising means for transferring said measurement aggregate from the first region to the second region.

17. The device according to claim 16, wherein the support is flat and impermeable to at least the intermediate mixture.

18. The device according to claim 14, wherein the receiving region comprises:
- a well for receiving the sample in the liquid phase and at least one incubation well connected to the receiving well for receiving said intermediate mixture, and
- the separating region comprises at least one reading well connected to the incubation well for separating the measurement aggregate.

19. The device according to claim 18, wherein the receiving region comprises a plurality of incubation wells connected, on one side, in parallel to a single receiving well and a plurality of reading wells connected respectively to the incubation wells.

20. The device according to claim 18, wherein the incubation well contains the metal reagent in the liquid phase, and the receiving well is connected to the incubation well by a channel which is leaktight to the sample in the liquid phase and to the reagent in the liquid phase, when the support is not vibrated, and allows said sample to pass when the support is vibrated.

21. The device according to claim 14,
- wherein the magnetic means is a conduit for circulating the intermediate mixture, which has a cross-section, and
- wherein the magnetic means is arranged in front of the detection means and the cross-section of said conduit is used for detection of said ferromagnetic mass by said detection means.

22. The device according to claim 14, wherein a generator of periodic oscillations is present and imparts periodic oscillations to the measurement aggregate and cooperates with the detection means.

23. The device according to claim 14, wherein an auxiliary magnetic generator is arranged at the detection means in order to increase the ferromagnetic mass of the measurement aggregate.

24. The process according to claim 1, wherein said contacting step includes incubating the sample with the reagent at a temperature other than that of the original sample and/or reagent.

25. The process according to claim 1, wherein the metal complexes of the reactive particles which have reacted with the analyte are confined, in the form of a measurement aggregate, and said aggregate is separated from the unreacted residual reactive particles simultaneously.

26. The process according to claim 1, wherein the measurement aggregate is separated from an intermediate medium in which the unreacted residual reactive particles remain, by moving the magnetic field used for confining the metal complexes, and said measurement aggregate is moved from and out of said intermediate medium.

27. The process according to claim 4, wherein the magnetic lines are mobile along a direction from said first area to said second area.

28. The process according to claim 12, wherein the periodic oscillations are generated by a gas jet impacting an edge of said flat support.

29. The device according to claim 14, wherein said means for bringing the sample and the reagent into contact includes means for incubating the sample with the reagent.

30. The device according to claim 22, wherein the generator propels a tangential gas flow against an edge of the support.

31. The device of claim 14, wherein the support does not react with the ligand or anti-ligand.

* * * * *